United States Patent [19]

Byrne et al.

[11] Patent Number: 4,575,556

[45] Date of Patent: Mar. 11, 1986

[54] BIFUNCTIONAL CHELATING AGENTS

[75] Inventors: Edmund F. Byrne, Alameda, Calif.; Glen L. Tolman, Chelmsford, Mass.

[73] Assignee: Medi-Physics, Inc., Emeryville, Calif.

[21] Appl. No.: 555,850

[22] Filed: Nov. 28, 1983

Related U.S. Application Data

[62] Division of Ser. No. 439,960, Nov. 8, 1982, Pat. No. 4,434,151.

[51] Int. Cl.$^4$ .......................................... C07C 333/32
[52] U.S. Cl. ...................................................... 549/63
[58] Field of Search ............................................ 549/63

[56] References Cited

U.S. PATENT DOCUMENTS 4,255,443 3/1981 McCully ................................. 549/63
4,411,909 10/1983 Gonella ................................. 549/63
4,434,151 2/1984 Byrne et al. .......................... 549/63

Primary Examiner—Delbert R. Phillips
Attorney, Agent, or Firm—Jon S. Saxe; George M. Gould; William H. Epstein

[57] ABSTRACT

Novel homocysteine thiolactone bifunctional chelating agents useful for chelating radionuclides to produce a radiodiagnostic agent for use in in vivo imaging and a method for producing this chelating agent.

4 Claims, No Drawings

BIFUNCTIONAL CHELATING AGENTS

This is a division of application Ser. No. 439,960 filed Nov. 8, 1982, now U.S. Pat. No. 4,434,151, issued Feb. 28, 1984.

BACKGROUND OF INVENTION

Scintigraphy and similar radiographic techniques are finding increasing application in biological and medical research and diagnostic procedures. Scintigraphy involves the use of radiopharmaceuticals having a radioactive material which upon introduction into a biological subject, becomes localized in specific organs, tissue or skeletal material desired to be imaged. When so localized, traces, plates or scintiphotos of the distribution of the radioactive material may be made by various radiation detectors. The resultant distribution of the radioactive material in the organ or tissue in which it is localized can be used to detect the presence of abberations, pathological conditions or the like.

In preparing the radiopharmaceutical, radionuclide chelating agents are utilized which will act as a bridge to connect the radioactive material such as a radioactive metal and the material which will localize in the organ, or tissue to be imaged. In general, effective chelating agents are desired which will couple the radionuclides to the material which will localize in the organ to be imaged.

SUMMARY OF THE INVENTION

In accordance with this invention, it has been discovered that novel compounds of the formula:

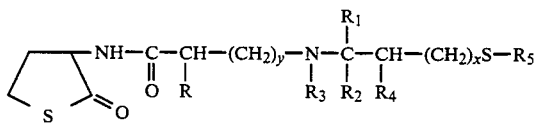

wherein R is hydrogen or lower alkyl, $R_1$ and $R_2$ are individually hydrogen or lower alkyl or taken together form oxo; $R_3$ is an amino protecting group where $R_1$ and $R_2$ are individually hydrogen or lower alkyl; $R_3$ is hydrogen where $R_1$ and $R_2$ taken together form oxo; $R_4$ is hydrogen or lower alkyl; $R_5$ is hydrogen or a thiol protecting group; x and y are integers from O to 2 are bifunctional chelating agents and as such can couple radionuclides to terminal amino containing compounds capable of localizing in an organ or tissue which is desired to be imaged. Hence, the compound of formula I can be used in preparing radiopharmaceuticals for in vivo diagnostic imaging.

DETAILED DESCRIPTION

The term "lower alkyl" as used throughout this application designates aliphatic saturated branched or straight chain hydrocarbon monovalent substituents containing from 1 to 7 carbon atom such as methyl, ethyl, isopropyl, n-propyl, n-butyl, etc. The term "lower alkoxy" as used throughout this specification designates lower alkoxy substituents containing from 1 to 7 carbon atoms such as methoxy, ethoxy, isopropoxy, etc. The term "halogen" designates all four halogens such as chlorine, fluorine, iodine, or bromine.

The term "aryl" as utilized herein designates a mononuclear aromatic hydrocarbon group which can be unsubstituted or substituted in one or more positions with a lower alkyl group such as phenyl or tolyl as well as polynuclear aromatic hydrocarbon groups which can be unsubstituted or substituted in one or more positions with a lower alkyl group such as napthyl, anthryl, phenanthryl, azulyl, etc. The preferred lower aryl group is phenyl. The term "aryl lower alkyl" designates aryl lower alkyl substituents where aryl and lower alkyl groups as defined above, particularly benzyl.

The term "lower alkanoyl" as used throughout this specification designates "lower alkanoyl" groups containing from 2 to 7 carbon atoms such as acetyl, propionyl, etc. The term "arylloweralkanoyl" designates monovalent arylloweralkanoyl groups where aryl and lower alkanoyl are defined as above with phenylacetyl being preferred. The term "aroyl" defines aroyl groups where the aryl group is defined as above with benzoyl being preferred.

As used herein, the term "thiol protecting group" includes all of the conventional groups which are commonly employed to protect the thiol moiety. Among these groups are included lower alkylaminocarbonyl such as ethylaminocarbonyl, loweralkanoylaminomethyl, aroylaminomethyl, t-butyl, triarylmethyl such as triphenylmethyl, aroyl such as benzoyl, aryloxycarbonyl such as phenoxycarbonyl, arylloweralkoxylcarbonyl, preferably arylmethoxycarbonyl such as benzyloxycarbonyl, lower alkoxycarbonyl such as t-butoxycarbonyl. Among the preferred lower alkanoylaminomethyl groups is aceteamidomethyl and among the preferred aroylaminomethyl is benzoylaminomethyl. The thiol protecting groups are removable by treatment with heavy metallic ions such as mercuric ions, technetium ions, silver ions, as well as any of the radioactive metals which form the complex. Anyof the conventional methods commonly employed in removing these thiol protecting groups can be utilized in accordance with this invention.

In accordance with this invention, the compound of formula I is prepared from a compound of the formula:

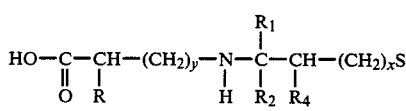

wherein R, $R_1$, $R_2$, $R_3$, $R_4$, x and y are as above. When $R_1$ and $R_2$ are other than oxo, the nitrogen group in the compound of formula II is protected with a conventional amino protecting group to produce a compound of the formula:

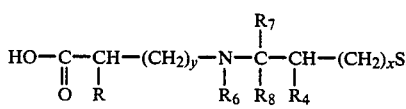

wherein x, y, R and $R_4$ are as above; $R_6$ is an amino protecting group; $R_7$ and $R_8$ are individually hydrogen or lower alkyl.

Any conventional method of converting a secondary amine to a protected amine can be utilized in converting the compound of formula II to the compound of formula II-A. Any of the conventional amino protecting groups which can be removed by conventional acid hydrolysis or catalytic hydrogenation can be utilized in this invention. Among the preferred amino protecting groups are included triarlymethyl such as trityl, aryl-loweralkoxycarbonyl such as benzyloxycarbonyl, lower alkoxycarbonyl such as t-butoxycarbonyl, aryl such as benzyl, etc. Any conventional method of preparing these protected amino groups can be utilized in accordance with this invention. Among these methods are reacting the compound of formula II where $R_1$ and $R_2$ are hydrogen or lower alkyl with the halide of the protecting group to be introduced into the compound of formula II. Any of the conditions conventional in such reactions can be utilized.

The compounds of formula II or II-A can be either free acids or the acid can be protected by esterification. The use of an ester increases the yield where either the compound of formulae II or II-A is reacted to introduce an amino protecting or a thiol protecting group. However, this ester group should be hydrolyzed before the compound of formulae II or II-A is reacted to form the compound of formula I. Any conventional method of ester hydrolysis can be used to form the free acid of formula I.

A thiol protecting group can be introduced if desired into the compound of formula II or IIA by conventional means. It has been found that best results as far as yields are achieved when the thiol group in the compound of formula II and formula IIa is protected with any of the groups hereinbefore mentioned. On the other hand, the reaction and production of the bifunctional chelate can be achieved without the use of a thiol protecting group.

The compounds of formulae II or II-A in their free acid form and when $R_1$ and $R_2$ are hydrogen or a lower alkyl, the amino group is protected with an amino protecting group and which may or may not contain a thiol protecting group can be converted to the compound of formula I by reaction with a compound of the formula:

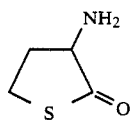

IV

This reaction is carried out by conventional amide formation. Any conventional means of reacting an organic carboxylic acid with an amine to form an amide can be utilized in this conversion to produce the compound of formula I. Generally, this reaction is carried out in the presence of an amide condensation agent such as a loweralkylhalo formate, i.e. ethylchloroformate or dicyclohexyl carbodiimide. When utilizing the alkyl chloro formate method, the amide formation occurs by means of a mixed anhydride since the alkylchloroformate forms an anhydride with the compound of formula II-A which then reacts with the amine group on the compound of formula IV to form the amide of formula I. Any of the conditions conventionally used in reacting an organic acid with an amine to form an amide through the use of a loweralkylhaloformate can be utilized in carrying out this procedure. On the other hand, when a coupling agent such as dicyclohexylcarbodiimide is utilized, any of the conditions conventionally utilized with such coupling agent can be used to produce the compound of formula I.

The compound of formula I can be converted to a bifunctional anionic chelate of the formula:

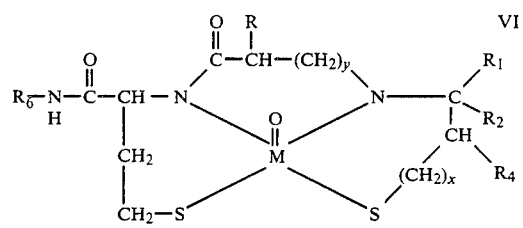

VI wherein $R_6$ is lower alkyl; $R_1$ and $R_2$ are individually hydrogen or lower alkyl or taken together form oxo; $R_4$, R, x and y are as above; M is a radioactive metal via the following intermediates:

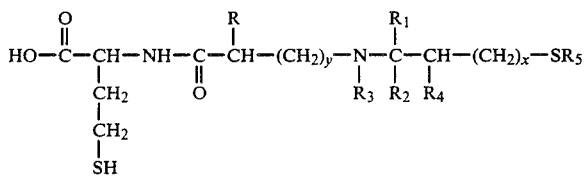

VII

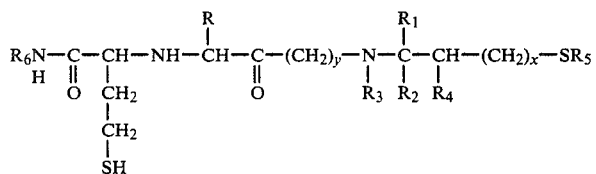

VIII

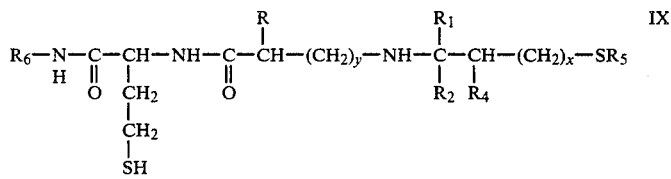

IX wherein M, R, $R_1$, $R_2$, x, y, $R_4$, $R_4$, $R_5$ and $R_6$ are as above, with the proviso that $R_3$ is an amino protecting group when $R_1$ and $R_2$ are individually hydrogen or lower alkyl; and with the further proviso that $R_3$ is hydrogen when $R_1$ and $R_2$ taken together form oxo.

The compound of formula I is converted to the compound of formula VII by treating the compound of formula I with a base. Any conventional strong inorganic base such as sodium hydroxide, ammonium hydroxide, potassium hydroxide, etc. can be utilized in carrying out this reaction. Any of the conditions conventional in hydrolysis with an alkali metal base can be used to carry out this reaction.

The compound of formulae I or VII can be converted to the compound of formula VIII by reacting either of these compounds with a compound of the formula:

$$R_6-NH_2 \qquad\qquad X$$

where $R_6$ is as above.

The compound of formulae VII is reacted with the compound of formula X utilizing the same conditions described in connection with the reaction of the compound of formula IV with the compound of formulae II or II-A to produce the compound of formula I. In fact, any conventional method of condensing a lower alkyl amine with an organic carboxylic acid to produce an amide can be utilized in carrying out this reaction.

The compound of formula I can also be reacted with the compound of formula X to produce a compound of formula VII. This reaction is carried out by mixing the compound of formula I and the compound of formula X together in an anhydrous inert organic solvent. Any conventional inert organic solvent can be utilized in carrying out this reaction with other solvents such as tetrahydrofuran being preferred. In carrying out this reaction, room temperature and atmospheric pressure are generally utilized.

In the next step, the compound of formula VIII where $R_3$ is an amino protecting group is converted to the compound of formula IX by treating the compound of formula VIII with an aqueous mineral acid or catalytic hydrogenation. Any conventional aqueous mineral acid such as a hydrohalic acid can be utilized in carrying out this reaction to remove protecting groups which are hydrolyzed by conventional acid hydrolysis. On the other hand when $R_3$ is an amino protecting group removable by hydrogenation, any conventional method of catalytic hydrogenation can be utilized to remove this protecting group and convert the compound of formula VIII to the compound of formula IX.

The compound of formulae IX where $R_1$ and $R_2$ do not form oxo, can be used to produce the anionic complex of formula VI either as a free base or in the form of its acid addition salt. Any conventional acid can be used in forming these salts. Among these acids are hydrochloric acid, phosphoric acid, acetic acid, propionic acid, citric acid, tartaric acid, etc.

The compound of formula IX is converted to the anionic complex of formula VI by reacting the compound of formula IX with a conventional salt of a radioactive metal. In forming the radioactive metal complex of formula X, any conventional radioactive isotope of technetium can be utilized. Among the radioactive isotopes are included technetium-99m. The aforementioned radioactive metals exist with coordination number of five in the complex of formula VI.

The compounds of formula II are known compounds and prepared from conventional protected amino acids of the formula:

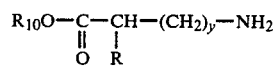

wherein R and y are as above and $R_{10}$ taken together with its attached oxygen atom form a hydrolyzable ester group such as a lower alkyl ester.

If in the compound of formula II, $R_1$ and $R_2$ are oxo, this compound is prepared by reacting the compound of formula XIII with a compound of the formula:

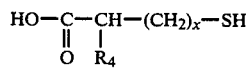

where x and $R_4$ are as above.

This reaction is carried out by amide condensation in the same manner as described in connection with the reaction of the compound of formulae II or II-A to produce a compound of formula I.

On the other hand where $R_1$ and $R_2$ in the compound of formula I are hydrogen or lower alkyl, the compound of formula II is produced by reacting the compound of formula XV with a compound of the formula

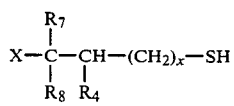

wherein $R_4$, $R_8$ and x are as above; and X is halogen.

The compound of formula XV is reacted with the compound of formula XIII utilizing any of the conventional techniques commonly employed in reacting primary amines with halides to produce secondary amines. In this manner, the compound of formula II wherein $R_1$ and $R_2$ are hydrogen or lower alkyl is produced. If it is desired to produce the compound of formula II in its free acid form, the reaction produced by reacting the compound of formula XIII with either the compound of formulae XIV or XV is subjected to conventional ester hydrolysis. On the other hand, the thiol group in the compounds of formulae XIV or XV can, if desired, be protected with a conventional thiol protecting group prior to reaction with the compound of formula XIII. In this manner, the compound of formula II is produced wherein the thiol group is protected by a conventional thiol protecting group.

In forming the complex of radioactive technetium with the compound of formula IX the technetium complex of formula I, the alkali metal salt of technetium-99m pertechnetate is reacted with the compound of formula IX in the presence of a reducing agent such as stannous chloride or sodium dithionite. The complex of formula VI can be prepared with the conventional salts of radioactive metals of technetium. Among these salts are the acetate, citrate and halide salts such as the chloride, bromide, fluoride and iodine salts of these radioactive metals. Among the technetium-99m pertechnetate salts are included the alkali metal salts such as the sodium salts or ammonium salts, or lower alkyl amine salts. The reaction of the compound of formula IX with the salt of the radioactive metal can be carried out in an aqueous medium at room temperature. The anionic complex of formula VI which has a charge of $-1$ can be formed in the aqueous medium in the form of a salt with a suitable cation such as ammonium cation, mono, di or tri-lower alkyl amine cation, etc. Any conventional salt of the anionic complex of formula VI with a pharmaceutically acceptable cation can be used in accordance with this invention. If it is desired to precipitate the anionic complex of formula VI, a salt is formed with a heavy cation such as tetraphenyl arsinate. Any conventional method of salt formation can be utilized to produce the chelate of formula VI as a salt. It is through the use of a precipitate with a heavy cation that this chelate can be characterized by structure.

In carrying out the reaction of the compound of formula IX with the salts of the radioactive metal to form the anionic complex of formula VI, the thiol protecting group is cleaved. Therefore, this reaction not only introduces the radioactive metal into the compound of formula VI but also cleaves the thiol protecting group. All of the aforementioned thiol protecting groups are cleaved by a reaction of salts of radioactive metals in accordance with this invention.

In forming the complex of formula VI, the radioactive material can have any suitable amount of radioactivity. In forming the radioactive anionic complexes of formula VI, it is generally preferred to form radioactive complexes in solutions containing radioactive concentrations of from about 0.01 mCi to 100 mCi per ml.

The complex of formula VI can be used for visualizing the organs such as the kidney for diagnosing disorders in these organs. In accordance with this invention, the anionic complex of formula I either as a anionic complex or as a salt with a pharmaceutically acceptable cation are administered in a single unit injectable dose. Any of the common carriers such as sterile saline solution, plasma, etc., can be utilized for preparing the injectable solution to diagnostically image various organs in accordance with this invention. Generally, the unit dose to be administered has a radioactivity of about 0.01 mCi to about 100 mCi, preferably 1 mCi to 20 mCi. The solution to be injected to unit dosage is from about 0.01 ml to about 1 ml. After intravenous administration, imaging of the organ in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of imaging for diagnostic purposes can be utilized in accordance with this invention.

The complexes of formula VI may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred mediums are normal saline and plasma.

The following examples are illustrative but not limitative of the invention. The percent (%) yields in the following examples are given based upon the mols of starting material.

EXAMPLE 1

N-(t-Butyloxycarbonyl)cysteamine-N-acetic acid

Cysteamine-N-acetic acid hydrochloride, 5.16 g (30 mmoles), is dissolved in 100 mL of deionized water and 10.0 mL (72 mmoles) of freshly distilled $Et_3N$ is added. N-t-butyloxycarbonyloxyimino-2-phenylacetonitrile, 7.5 g (30 mmoles), is dissolved in 50 mL of dioxane and added in one portion to the cysteamine solution. The reaction mixture is stirred at room temperature overnight. The solution is reduced to 50 mL by rotary evaporation and poured into 200 mL EtOAc. The EtOAc phase is extracted with 3 portions of 100 mL saturated $NaHCO_3$. The $NaHCO_3$ portions are combined and the pH is lowered to 3.5 by addition of solid citric acid. The yellow product is extracted into 250 mL of EtOAc. The EtOAc is dried over anhydrous $Na_2SO_4$ and removed by rotary evaporation. After drying under vacuum overnight, 4.25 g (60% yield) of the yellow glassy compound, N-(t-butyloxycarbonyl)cysteamine-N-acetic acid, is obtained.

EXAMPLE 2

N-(t-butyloxycarbonyl),N-(2-mercaptoethyl)glycyl homocysteine thiolactone (a) Mixed Anhydride Method N-(t-butyloxycarbonyl)cysteamine-N-acetic acid, 1.50 g (6.4 mmoles), is dissolved in 50 mL $CH_2Cl_2$ by addition of 1.0 mL (7.2 mmoles) of freshly distilled $Et_3N$. This solution is cooled to 0° C. on an ice bath under an argon atmosphere and 0.85 mL (6.5 mmoles) of isobutylchloroformate is added dropwise over a period of five minutes. The solution turns orange-red after 15 minutes of stirring. A solution of 1.16 g (7.5 mmoles) of homocysteine thiolactone hydrochloride dissolved in 100 mL of $CH_2Cl_2$ by addition of 2.2 mL (15.8 mmoles) of $Et_3N$ is added dropwise over 15 minutes. The solution is stirred at 0° C. for 4 hours and left to stir at room temperature overnight. The $CH_2Cl_2$ solution is extracted with $2 \times 100$ mL of 5% by weight aqueous citric acid, $2 \times 100$ mL of saturated $NaHCO_3$, and 100 mL saturated NaCl. The $CH_2Cl_2$ is dried over anhydrous $Na_2SO_4$ and removed by rotary evaporation. After drying under vacuum overnight, 1.5 g (75% yield) of a white glass is obtained. TLC in 5% by volume methanol-95% by volume chloroform showed the major spot at Rf=0.4. The white glass product was purified by silica gel chromatography to yield 0.9 g (45% yield) of N-(t-butyloxycarbonyl), N-(2-mercaptoethyl)glycyl homocysteine thiolactone as a white crystalline solid.

(b) Carbodiimide Method

N-(t-butyloxycarbonyl)cysteamine-N-acetic acid, 1.41 g (6 mmoles); 1-hydroxybenzotriazole, 1.22 g (9 mmoles); homocysteine thiolactone hydrochloride, 1.0 g (6.5 mmoles); and 2.5 mL (14 mmoles) of freshly distilled $Et_3N$ are dissolved in 50 mL of $CH_2Cl_2$. The solution is cooled to 0° C. and a solution of 1.24 g (6 mmoles) of N,N'-dicyclohexylcarbodiimide in 10 mL $CH_2Cl_2$ is added in one portion. The solution is stirred on ice for 4 hours and left to stir at room temperature overnight. The N,N'-dicyclohexylurea is filtered and the $CH_2Cl_2$ solution is extracted with $2 \times 100$ mL 5% by weight aqueous citric acid, $2 \times 100$ mL saturated $NaHCO_3$, and 100 mL saturated NaCl. The $CH_2Cl_2$ is dried over anhydrous $Na_2SO_4$ and removed by rotary evaporation. After drying under vacuum, 2.1 g of a light pink crystalline product is obtained.

TLC in 5% methanol-95% chloroform showed the major spot at Rf=0.4. The product was purified by silica gel chromatography to yield 0.75 g (37.5% yield) of the white crystalline solid N-(t-butyloxycarbonyl), N-(2-mercaptoethyl)glycyl homocysteine thiolactone.

EXAMPLE 3

N-(t-butyloxycarbonyl), N-(2-mercaptoethyl)glycyl N'-methylhomocysteinamide

N-(t-butyloxycarbonyl), N-(2-mercaptoethyl)glycol homocysteine thiolactone, 1.0 g (3 mmoles), is dissolved in 25 mL THF and cooled to 0° C. The solution is saturated with methylamine by bubbling methylamine gas through for 10 minutes. The reaction is stirred for 30 minutes and the solvent removed by rotary evaporation. After drying overnight under vacuum, 1.09 g (100% yield) of N-(t-butyloxycarbonyl), N-(2-mercaptoethyl)glycyl N'-methylhomocysteinamide is obtained as a white glass.

EXAMPLE 4

N-(2-mercaptoethyl)glycyl N'-methylhomocysteinamide hydrochloride

N-(t-butyloxycarbonyl), N-(2-mercaptoethyl)glycyl N'-methylhomocysteinamide, 1.09 g (3 mmoles), is dissolved in 25 mL THF and cooled to 0° C. HCl gas is bubbled through the solution. After one minute, a white precipitate begins to form. The bubbling is continued for 15 minutes and the mixture is stirred for 15 more minutes. The white precipitate is filtered and washed with THF being careful not to dry by air suction. The still wet white product is vacuum dried overnight to yield 550 mg (60% yield) of white, crystalline N-(2-mercaptoethyl)glycyl N'-methylhomocysteinamide hydrochloride.

EXAMPLE 5

Tetraphenylarsonium salt of [2-[[1-(2mercaptoethyl)-2-(methylamino)-2-oxoethyl]amino]-N-(2-mercaptoethyl)glycinato-N,N',S,S']oxotechnetate-99

$NH_4$ $^{99}TcO_4$, 50 mg (0.28 mmoles), and N-(2-mercaptoethyl)glycyl N'-methylhomocysteinamide hydrochloride, 160 mg (0.53 mmoles), were dissolved in 2 mL of 1:1 parts by volume EtOH and 2N NaOH mixture. A solution of 50 mg (0.29 mmoles) of $Na_2S_2O_4$ in 1.0 mL 2N NaOH was added dropwise to the stirred solution turning it from clear to deep orange. Electrophoresis of the orange solution in tris-bartital-sodium barbital buffer at pH 8.8 run at 600 V for 45 minutes on paper showed that the orange complex migrated 7.2 cm toward the anode. Electrophoresis indicated a small amount (<1%) of black $TcO_2$ that stayed at the spotting point but showed not $TcO_4^-$ at its characteristic 12.5 cm migration. The orange solution was filtered to remove the black, insoluble $TcO_2$ and was added to a solution of 150 mg (0.36 mmoles) of $Ph_4AsCl \cdot H_2O$ in 2.0 mL of water. An orange oil separated and was dissolved by adding about 2 mL of methanol. This solution was left to stand in an open beaker for several days. After one week orange crystals formed at the bottom of the beaker and the once dark orange solution was not faintly yellow. The crystals were filtered, washed with a small amount of cold water followed by $Et_2O$, and dried by air suction to yield 180 mg (86% yield) of tetraphenylarsonium salt of [2-[[1-(2-mercaptoethyl)2-(methylamino)-2-oxoethyl]amino]-N-(2-mercaptoethyl)glycinato-N,N',S,S']oxotechnetate-99 as bright orange crystals. Dark orange plate-like crystals suitable for x-ray structure determination were grown by slow evaporation of an ethanol-chloroform solution of the product.

EXAMPLE 6

[2-[[1-(2mercaptoethyl)-2-(methylamino)-2-oxoethyl]amino]-N-(2-mercaptoethyl)glycinato-N,N',S,S']oxotechnetate-99m 1. Dithionite Reduction at pH 13.3

N-(2-mercaptoethyl)glycyl N'-methylhomocysteinamide hydrochloride, 5 mg (0.17 mmoles), is dissolved in 1.0 mL absolute EtOH and 1.0 mL 1.0N NaOH. A 1.0 mL generator eluant of $^{99m}TcO_4^-$ (5 to 50 mCi) in saline is added. Then 0.5 ml of a dithionite solution, prepared by dissolving 100 mg $Na_2S_2O_4$ per mL of 1.0N NaOH, is added. After 15-30 minutes, the [2-[[1-(2mercaptoethyl)-2-(methylamino)-2-oxoethyl]amino]-N-(2-mercaptoethyl)glycinato-N,N',S,S']oxotechnetate-99m is prepared [$^{99m}$Tc-MGHA complex]. This solution of the $^{99m}$Tc-MGHA complex is buffered by addition of 1.0 mL of 1N HCl and 4.0 mL of 0.1M $NaH_2PO_4$ pH 4.5 buffer. The labeling of this complex is determined by electrophoresis in tris-barbital-sodium barbital buffer at pH 8.8 and was run at 600 V for 45 minutes on paper. The $^{99m}$Tc-MGHA complex migrates 7.2 cm toward the anode under these electrophoretic conditions. The possible impurities, $^{99m}TcO_2$ and $^{99m}TcO_4^-$, are easily distinguished from the $^{99m}$Tc-MGHA comples by this electrophoresis method because the unreduced $^{99m}TcO_4^-$ migrates 12.5 cm toward the anode while $^{99m}TcO_2$ remains at the origin.

2. Stannous Reduction at pH 6.5

N-(2-mercaptoethyl)glycyl N'-methylhomocysteinamide hydrochloride, 5 mg (0.17 mmoles), is dissolved in 1.0 mL EtOH and 1.0 mL 0.1M sodium acetate at pH 5.5. A 1.0 mL generator eluant of $^{99m}TcO_4^-$ (5–50 mCi) in saline is added. Then 0.2 ml of stannous solution, prepared by dissolving 2.0 mg $SnCl_2 \cdot 2H_2O$ per mL of ethanol, is added to produce [2-[[1-(2mercaptoethyl)-2-(methylamino)-2-oxoethyl]amino]-N-(2-mercaptoethyl)glycinato-N,N',S,S']oxotechnetate-99m. After 15-30 minutes, the labeling efficiency is determined by electrophoresis as described under the dithionite reduction method above with the same results.

EXAMPLE 7

N-[2-(S-acetamidomethyl)mercaptopropionyl]glycine 2-mercaptopropionylglycine, 20.0 g (122.6 mmoles), and N-hydroxymethyl-acetamide, 12.0 g (134.8 mmoles), are dissolved in 200 ml of deionized water. The solution is cooled on an ice bath and 100 ml of conc. HCl is added in one portion. The mixture is stirred on ice for one hour and at room temperature overnight. A white precipitate begins to form within 1–2 hours.

The reaction mixture is cooled on ice for 4 hours. The white precipitate is filtered, washed with a few mls of ice-cold water, then 2×200 ml $Et_2O$. The product is dried by air suction for one hour and uncer vacuum overnight to yield 14.4 g (50.2% yield) of the white, crystalline product N-[2-(S-acetamidomethyl)mercaptopropionyl]glycine.

EXAMPLE 8

N-[2-(S-benzamidomethyl)mercaptopropionyl]glycine 2-mercaptopropionylglycine, 5.0 g (30.6 mmoles), and N-hydroxymethylbenzamide, 5.0 g (33.1 mmoles), are dissolved in 100 ml of deionized water. The solution is cooled on an ice bath and 50 ml of conc. aqueous HCl is added in one portion. The mixture is stirred on ice for one hour and at room temperature overnight. A white precipitate begins to form within thirty minutes. After this period the reaction mixture is cooled on ice for 4 hours. The white precipitate is filtered, washed with ice-cold water, then 2×200 ml Et$_2$O. The product is dried by air suction for an hour and under vacuum overnight to yield 8.4 g (94.4% yield) of the white, crystalline product N-[2-(S-benzamidomethyl)mercaptopropionyl]glycine.

EXAMPLE 9

N-[2-(S-acetamidomethyl)mercaptopropionyl]glycyl homocysteine thiolactone

1. Carbodiimide Method

N-[2-(S-acetamidomethyl)mercaptopropionyl]glycine, 2.35 g (10 mmoles), homocysteine thiolactone hydrochloride, 1.55 g (10 mmoles), 1-hydroxybenzotriazole, 2.1 g (15 mmoles), and 4.5 ml of Et$_3$N are dissolved in 150 ml CH$_2$Cl$_2$. A solution of 2.0 g (9.7 mmoles) of dicyclohexylcarbodiimide in 50 ml CH$_2$Cl$_2$ is then added in one portion and the mixture is stirred overnight.

The reaction mixture is filtered to remove the white precipitate which is dicyclohexylurea. The solvent is removed by rotary evaporation. After this, the residue is vacuum dried overnight, and 7.8 g of crude material remains. The crude product is dissolved in 5 ml of MeOH:CHCl$_3$ (5/95 parts by volume) and loaded on a silica gel column of 8 cm diameter and 10 cm height requiring 250 g of silica gel. The column is eluted with MeOH:CHCl$_3$ (5/95 parts by weight) and 5 ml fractions are collected. The product at R$_f$=0.3 on TLC in MeOH:CHCl$_3$ (10/90 parts of volume) elutes in fractions 110–190. These fractions are combined and the solvent is removed by rotary evaporation. After removal of solvent, the residue is dried under vacuum overnight, 2.0 g (60.6% yield) of N-[2-S-acetamidomethyl)mercaptopropionyl]glycyl homocysteine thiolactone as a white glass is obtained.

2. Mixed Anhydride Method

N-[2-(S-acetamidomethyl)mercaptopropionyl]glycine, 7.05 g (30 mmoles), is dissolved in 150 ml CH$_2$Cl$_2$ by addition of 7.5 ml (54 mmoles) of Et$_3$N. The solution is cooled to −15° C. on a dry ice-acetone bath. Isobutylchloroformate, 3.9 ml (30 mmoles), is added dropwise over a 5 minute period. The temperature is maintained at −15° C. throughout the addition. After the addition of isobutylchloroformate is completed, the reaction is stirred for 3–5 minutes. A solution of 4.65 g (30 mmoles) of homocysteine thiolactone hydrochloride and 4.2 ml (30 mmoles) of Et$_3$N in 100 ml of CH$_2$Cl$_2$ is added dropwise over a period of 15–30 minutes at a rate that maintains the temperature at −15° C. The solution is then stirred at −15° C. for one hour and at room temperature overnight.

The white precipitate that forms is filtered, washed with a small amount of CH$_2$Cl$_2$, dried by air suction for one hour and under vacuum overnight. This yields 3.2 g (32% by weight yield) of N-[2-(S-acetamidomethyl)-mercaptopropionyl]glycyl homocysteine thiolactone as a fine, white powder. TLC on silica gel in MeOH:CHCl$_3$ (10/90 parts by volume) shows a single spot at R$_f$=0.3.

A second crop of N-[2-(S-acetamidomethyl)mercaptopropionyl]glycyl homocysteine thiolactone 700 mg (40% overall yield) of TLC-pure product was obtained by evaporating the filtrate, dissolving the residue in a minimum of MeOH, and letting the solution stand for two days.

EXAMPLE 10

N-[2-(S-benzamidomethyl)mercaptopropionyl]glycyl homocysteine thiolactone

1. Carbodiimide Method

N-[2-(S-benzamidomethyl)mercaptopropionyl]glycine, 2.96 g (10 mmoles), homocysteine thiolactone hydrochloride, 1.55 g (10 mmoles), 1-hydroxybenzotriazole, 2.1 g (15 mmoles), and 4.5 ml Et$_3$N is dissolved in 100 ml CH$_2$Cl$_2$. A solution of 2.0 g (9.7 mmoles) of dicyclohexylcarbodiimide in 50 ml CH$_2$Cl$_2$ is then added in one portion and the mixture is stirred overnight.

The dicyclohexylurea that precipitates is filtered and the CH$_2$Cl$_2$ solution is extracted with 2×200 ml 10% by weight aqueous HCl, 2×200 ml saturated NaHCO$_3$, and 200 ml saturated NaCl. The CH$_2$Cl$_2$ layer is dried over anhydrous Na$_2$SO$_4$ and removed by rotary evaporation. The residue is dried under vacuum overnight to yield 2.0 g of a white glass.

The crude product is dissolved in 3.0 ml of MeOH:CHCl$_3$ (5/95 parts by volume) and loaded on a silica gel column of 4.5 cm diameter and 12.5 cm height requiring 100 g of silica gel. The column is eluted with MeOH:CHCl$_3$ (5/95 parts by volume) and 4 ml fractions are collected. The product at R$_f$=0.4 on TLC in MeOH:CHCl$_3$ (10/90 parts by volume) elutes in fractions 51–70. The fractions are combined and the solvent is removed by rotary evaporation. After the residue is dried under vacuum overnight, 1.0 g (26.3% yield) of the white glass N-[2-(S-benzamidomethyl)-mercaptopropionyl]glycyl homocysteine thiolactone is obtained.

2. Mixed Anhydride Method

N-[2-(S-benzamidomethyl)mercaptopropionyl]glycine, 2.96 g (10 mmoles) is dissolved in 100 ml CH$_2$Cl$_2$ by addition of 3.0 ml (22 mmoles) of Et$_3$N. The solution is cooled to −15° C. on a dry ice-acetone bath. Isobutylchloroformate, 1.3 ml (10 mmoles), is added dropwise over a 5 minute period. The temperature is maintained at −15° C. throughout the addition. After the addition of isobutylchloroformate is completed, the reaction is stirred for 3–5 minutes. A solution of 1.55 g (10 mmoles) of homocysteine thiolactone hydrochloride and 1.4 ml (10 mmoles) of Et$_3$N in 50 ml CH$_2$Cl$_2$ is added dropwise over a period of 15–30 minutes. The temperature is maintained at −15° C. throughout the addition. The solution is then stirred at −15° C. for one hour and at room temperature overnight.

The CH$_2$Cl$_2$ solution is washed with 2×200 ml 10% by volume aqueous HCl, 2×200 ml saturated NaHCO$_3$, and 200 ml saturated NaCl. The CH$_2$Cl$_2$ layer is dried over anhydrous Na$_2$SO$_4$ and removed by rotary evaporation. The residue is dried under vacuum overnight to yield 2.7 g (71.0% yield) of N-[2-(S-benzamidomethyl)-mercaptopropionyl]glycyl homocysteine thiolactone as a white glass.

EXAMPLE 11

N-[2-(S-acetamidomethyl)mercaptopropionyl]glycyl N-methylhomocysteinamide

N-[2-(S-acetamidomethyl)mercaptopropionyl]glycyl homocysteine thiolactone, 1.0 g (3 mmoles), is suspended in 200 ml THF. Methylamine gas is bubbled vigorously through the suspension. Most of the white starting material goes into solution in 5-10 minutes. The gas is bubbled for 15 minutes more at a slow rate. TLC on silica gel in MeOH:CHCl$_3$ (15/85 parts by volume) shows that the reaction is complete. The excess CH$_3$NH$_2$ and also THF is removed by rotary evaporation. After the residue is dried under vacuum overnight, 1.1 g (100% yield) of the white glass N-[2-(S-acetamidomethyl)mercaptopropionyl]glycyl N-methylhomocysteinamide is obtained.

EXAMPLE 12

By the procedure of Example 11 N-[2-(S-benzamidomethyl)mercaptopropionyl]glycyl homocysteine thiolactone, converted to N-[2-(S-benzamidomethyl)mercaptopropionyl]glycyl N-methylhomocysteinamido.

EXAMPLE 13

Tetraphenylarsonium salt of [1-[[1-(2-mercaptoethyl)-2-(methylamino)-2-oxoethyl]amino]-N-(2-mercapto-1-1-oxopropyl)glycinato-N,N',S,S']oxotechnetate-99

NH$_4$$^{99}$TcO$_4$, 50.3 mg (0.28 mmoles), and 200.1 mg (0.55 mmoles) of N-[2-(S-acetamidomethyl)mercaptopropionyl]glycyl N-methylhomocysteinamide, were dissolved in 5.0 ml of 1:1 parts of volume EtOH:2-NNaOH. A solution of 60 mg (0.35 mmoles) Na$_2$S$_2$O$_4$ in 1.0 ml 2NNaOH was added dropwise. A bright yellow solution resulted and the solution turned dark orange after sitting for one hour. Electrophoresis of the orange solution was then run in barbital buffer at pH 8.8 at 600 V for 45 minutes on paper. The orange complex migrated 6.9 cm toward the anode indicating an anionic complex. No TcO$_2$ or TcO$_4$ impurities, which come at 0.0 and 12.5 cm, respectively, were observed. A solution of 250 mg (0.60 mmoles) of Ph$_4$AsCl.H$_2$O in 2.0 ml H$_2$O was added to the orange solution and it was left undisturbed overnight. The next day orange plates had formed at the bottom of the vial and the solution had only a light yellow color. The product was filtered, washed with water, and dried by air suction overnight to yield 158.8 mg (72.2% yield) of the tetraphenylarsonium salt of [1-[[1-(2-mercaptoethyl)-2-(methylamino)-2-oxoethyl]amino]-N-(2-mercapto-1,1-oxopropyl)glycinato-N,N',S,S']oxotechnetate-99 as goldenorange plates.

EXAMPLE 14

1. Dithionite Reduction at pH 13

N-[2-(S-acetamidomethyl)mercaptopropionyl]glycyl N-methylhomocysteinamide, 20 mg (0.55 mmoles), is dissolved in 2.0 ml 1:1 parts by volume of EtOH and 1NNaOH. A 0.5 ml generator eluant of $^{99m}$TcO$_4$−(5 mCi) is added. Then 0.5 ml of a dithionite solution, prepared by dissolving 100 mg Na$_2$S$_2$O$_4$ per ml of 1NNaOH, is added. The vial is left to stand for 30 minutes. Electrophoresis shows an anionic complex which is [1-[[1-(2-mercaptoethyl)-2-(methylamino)-2-oxoethyl]amino]-N-(2-mercapto-1,1-oxopropyl)glycinato-N,N',SS']oxotechnetate-99m and also shows the absence of the possible impurities $^{99m}$TcO$_2$ and $^{99m}$TcO$_4$−.

2. Stannous Reduction at pH 6.5

N-[2-(S-acetamidomethyl)mercaptopropionyl]glycyl homocysteinamide, 20 mg (0.55 mmoles), is dissolved in 1.0 ml 0.1M sodium acetate pH 4.5 buffer and 1.0 ml EtOH. A 0.5 ml generator eluant of $^{99m}$TcO$_4$-(5 mCi) is added. Then 0.2 ml of a stannous solution, prepared by dissolving 2.0 mg SnCl$_2$.2H$_2$O per ml EtOH, is added. The vial is left to stand for 30 minutes. Electrophoresis shows an anionic complex which is [1-[[1-(2-mercaptoethyl)-2-(methylamino)-2-oxoethyl]amino]-N-(2-mercapto-1-1-oxopropyl)glycinato-N,N',SS']oxotechnetate-99m.

EXAMPLE 15

By both the dithionite reduction at pH 13 procedure in Example 14 and the stannous reduction at pH 6.5 in Example 14, N-[2-(S-benzamidomethyl)mercaptopropionyl]glycyl N-methylhomocysteinamide is converted to [1-[[1-2-mercaptoethyl)-2-(methylamino)-2-oxoethyl]amino]-N-[2-mercapto-1-1-oxopropyl)glycinato-N,N',S,S']oxotechnetate-99m.

EXAMPLE 16

The $^{99m}$Tc complex used for the animal studies was prepared in Example 6 following both methods of reduction, stannous chloride or dithionite. The $^{99m}$Tc-MGHA complexes labeled by either reduction method were tested in animals. The mass concentrations of the $^{99m}$Tc complex administered to test animals were approximately 0.04 mg/kg body weight for rabbits and 13.0 mg/kg body weight for mice. The radioactivity administered to rabbits and mice were about 0.5 mCi and 1.5 mCi respectively. The pH of the injectant solution was approximately 5 to 6.

Nonanesthetized and nonfasted male rabbits (New Zealand White) weighing 3.0–3.5 kg were restrained in dorsal recumbancy approximately 2–3 cm from the face of the gamma camera. After intravenous administration of 0.1 mL of the $^{99m}$Tc-labeled complex solution in the marginal ear vein, anterior images were stored by a dedicated computer during injection, and 5, 10, 15, 20 and 30 minutes following administration. Relative counts per minute (cpm) versus time curves (uncorrected for $^{99m}$Tc decay) were determined from quantification of regional areas of interest (RAI) obtained from computer displayed images for $^{99m}$Tc complex.

Nonfasted male mice (1CR strain) weighing 20–24 grams were administered in the tail vein with 0.2 mL of a $^{99m}$Tc-complex solution. At 15, 30, 60 minutes post administration groups of four animals were sacrificed by cervical dislocation and selected organs removed for $^{99m}$Tc assay in a gross ionization counting chamber. The percentage of the injected dose corrected for $^{99m}$Tc decay was calculated for the various organs at each sacrifice time.

The RAIs obtained from the gamma camera images for animals administered with $^{99}$Tc-complex (SnCl$_2$ reduction method) and $^{99m}$Tc-complex (dithionite reduction method) showed significant count densities in regions where the right and left kidneys were visualized. No other apparent anatomical structures were clearly delineated. The organ distribution of $^{99}$m-Tc activity in mice after administration of $^{99m}$Tc-complex indicated fast clearance out of the body within the first 15 minutes. Subsequent sacrifice times greater than 15 minutes post injection showed little kidney uptake. Although kidney uptake of activity was declining at the various time intervals examined, the total remaining activity (% injected dose) in each test animal was approximately one-half of the injected dose at 30 minutes which indicated a rapid excretion of activity from the body. This indirect evidence suggests possible kidney clearance of $^{99m}$Tc in test animals administered $^{99m}$Tc-complex.

EXAMPLE 17

The $^{99m}$Tc-complex prepared via a dithionite reduction of Example 6 was administered to male albino rabbits weighing 3.0–3.5 kg. The drug was injected into the marginal ear vein. The mass of drug administered was equivalent to ~0.04 mg/kg while the volume injected was 0.1 mL. The administered dose was ~0.5 mCi. Each test animal was restrained in dorsal recumbancy approximately 2–3 cm from the face of the gamma camera. Immediately after injection, 100–500 k counts were obtained from the gamma camera and stored on floppy disc. The computer controlled the maximum number of counts that could be stored per image. Sequential images were obtained and stored on disc at 5, 10, 15, 20 and 30 minutes following administration.

After all images were stored, quantitative image analysis was utilized to obtain count densities in regional areas of interest (RAI). The RAIs were delineated as distinct anatomical structures. Three distinct areas were observed. The left and right kidneys and the bladder were clearly defined.

EXAMPLE 18

A $^{99m}$Tc-complex prepared via a stannous chloride reduction of Example 6 was administtered to male albino rabbits weighing 3.0–3.5 kg. The route of administration and the methods for evaluation of this test drug are described in Example 17.

EXAMPLE 19

A $^{99m}$Tc-MHGA complex prepared via a dithionite reduction of $^{99m}$TcO$_4^-$ of Example 6 was administered to female albino mice weighing 20–24 gm. The test drug was administered through the lateral tail vein at a mass dose of approximately 13.0 mg/kg in a volume of 0.2 mL. The corresponding radioactive dose administered to each animal was 1.5 mCi. After injection, groups of four animals were sacrificed (cervical dislocation) at 15, 30 and 60 minutes. The liver, kidney, lung, heart, stomach and intestines (small and large) were removed and assayed for $^{99m}$Tc activity in a gross ionization counting chamber. Also, the tails and remaining carcasses were individually assayed for $^{99m}$Tc activity.

Knowing the amount of $^{99m}$Tc activity administered (assaying for $^{99m}$Tc in the syringe before and after injection) and the amount assayed in the various organs, the percentage of injected dose (% ID) was calculated as:

$$\% \text{ ID} = \frac{\text{Ci of activity in organ}}{\text{Ci of activity injected}} \times 100\%$$

All activities (Ci) were initially corrected for $^{99m}$Tc decay back to a fixed starting time using the standard first order differential equation for decay correction (see below):

$$N_1 = N_0 e^{-(0.693/T_{\frac{1}{2}})t}$$

where $N_0$ and $N_1$ are initial and final activities (Ci) respectively. The half-life ($T_{\frac{1}{2}}$) for $^{99m}$Tc decay is 6.02 hr. The value of t is the elapsed time (hrs.) for the correction.

The results of $^{99m}$Tc uptake in various organs and tissues in mice administered $^{99m}$Tc-MGHA labeled via a dithionite reduction is given in Table 1.

EXAMPLE 20

A $^{99m}$Tc-MGHA complex prepared via a stannous chloride reduction of $^{99m}$TcO$_4^-$ of Example 6 was administered to female albino mice weighing 20–24 gm. The same methods and procedures given in Example 19 were used to calculate the % ID for each organ. The results are given in Table 2.

TABLE 1

Organ Uptake of $^{99m}$Tc in Mice After Intravenous Administration of $^{99m}$Tc-MGHA (Dithionite Reduction)

| Organ | (% Injected Dose) Time After Injection | | |
|---|---|---|---|
| | 15 min. | 30 min. | 60 min. |
| Liver | 11.3 ± 1.0[1] | 7.6 ± .9 | 10.2 ± 1.6 |
| Spleen | N.D.[2] | N.D. | N.D. |
| Kidney | 3.1 ± .6 | 3.4 ± .5 | 3.9 ± .6 |
| Heart | N.D. | N.D. | N.D. |
| Lung | .9 ± .2 | .3 ± .1 | .5 ± .3 |
| Stomach | .3 ± .01 | .1 ± .1 | .8 ± .9 |
| Carcass | 21.9 ± 2.9 | 13.4 ± 5.3 | 18.3 ± 2.5 |
| Intestines | 16.8 ± 3.0 | 20.5 ± 2.0 | 16.9 ± 1.4 |
| Tail | 1.7 ± 1.0 | .3 ± .1 | 1.1 ± .4 |

[1]Average of four animals ± standard deviation.
[2]N.D. = no detectable activity.

TABLE 2

Organ Uptake of $^{99m}$Tc in Mice After Intravenous Administration of $^{99m}$Tc-MGHA (SnCl$_2$ Reduction)

| Organ | (% Injected Dose) Time After Injection | | |
|---|---|---|---|
| | 15 min. | 30 min. | 60 min. |
| Liver | 13.3 ± 5.4[1] | 6.1 ± .9 | 7.7 ± 2.0 |
| Spleen | N.D.[2] | N.D. | N.D. |
| Kidney | 3.3 ± .9 | 1.6 ± .4 | 2.3 ± .8 |
| Heart | N.D. | N.D. | N.D. |
| Lung | .9 ± .4 | .2 ± .2 | .6 ± .3 |
| Stomach | .3 ± .4 | .6 ± .9 | .1 ± .2 |
| Carcass | 17.4 ± 2.8 | 5.7 ± 2.9 | 12.4 ± 5.1 |
| Intestines | 28.7 ± 6.1 | 27.3 ± 7.0 | 29.3 ± 10.4 |
| Tail | 1.4 ± .7 | .14 ± .2 | .7 ± .3 |

[1]Average oF four animals ± standard deviation.
[2]N.D. = No detectable activity.

We claim:

1. A compound of the formula:

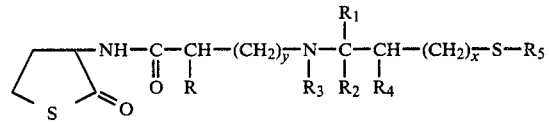

wherein R is hydrogen or lower alkyl; R$_1$ and R$_2$ are individually hydrogen or lower alkyl or taken together form oxo; R$_3$ is an amino protecting group where R$_1$ and R$_2$ are individually hydrogen or lower alkyl; R$_3$ is hydrogen when R$_1$ and R$_2$ taken together form oxo; R$_4$ is hydrogen or lower alkyl, R$_5$ is hydrogen or a thiol protecting group; and x and y are integers from 0 to 2.

2. The compound of claim 1 wherein said compound is N-(t-butyloxycarbonyl), N-(2-mercaptoethyl)glycyl homocysteine thiolactone.

3. The compound of claim 1 wherein said compound is N-[2-(S-acetamidomethyl)mercaptopropionyl]glycyl homocysteine thiolactone.

4. The compound of claim 1 wherein said compound is N-[2-(S-benzamidomethyl)mercaptopropionyl]glycyl homocysteine thiolactone.

* * * * *